United States Patent
Foster et al.

(10) Patent No.: US 6,627,737 B1
(45) Date of Patent: Sep. 30, 2003

(54) FACTOR IX PURIFICATION METHODS

(75) Inventors: W. Barry Foster, Chelmsford, MA (US); Robert J. Costigan, Boxford, MA (US); Duane Bonam, Amesbury, MA (US); Mary B. Switzer, Andover, MA (US); Rochelle Walsh, North Reading, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 08/953,143

(22) Filed: Oct. 17, 1997

Related U.S. Application Data

(63) Continuation of application No. 08/472,823, filed on Jun. 7, 1995, now Pat. No. 5,714,583.

(51) Int. Cl.$^7$ .................. C07K 1/14; C07K 14/745
(52) U.S. Cl. ................ 530/384; 530/412; 530/415; 530/416
(58) Field of Search ................. 530/344, 412, 530/415, 416, 384

(56) References Cited

U.S. PATENT DOCUMENTS

| | | | |
|---|---|---|---|
| 4,411,794 A | 10/1983 | Schwinn et al. | 210/670 |
| 4,447,416 A | 5/1984 | Menache-Aronson et al. | 424/101 |
| 4,721,572 A | 1/1988 | Jordan | 210/635 |
| 4,725,673 A | 2/1988 | Herring | 530/381 |
| 4,786,726 A | 11/1988 | Smith | 530/381 |
| 4,831,118 A | 5/1989 | Zimmerman et al. | 530/383 |
| 4,981,952 A | 1/1991 | Yan | 530/384 |
| 5,055,557 A | 10/1991 | Zimmerman | 530/381 |
| 5,061,789 A | 10/1991 | Moller et al. | 530/381 |
| 5,071,961 A | 12/1991 | Kraus et al. | 530/384 |
| 5,118,614 A | 6/1992 | Rybak et al. | 435/13 |
| 5,281,661 A | 1/1994 | Linnau et al. | 525/54.1 |
| 5,378,365 A | 1/1995 | Arrighi et al. | 210/635 |
| 5,409,990 A | 4/1995 | Linnau et al. | 525/54.1 |
| 5,714,583 A * | 2/1998 | Foster et al. | 530/384 |

FOREIGN PATENT DOCUMENTS

| | | | |
|---|---|---|---|
| EP | 0 317 376 A1 | 10/1988 | C07K/3/18 |
| EP | 0 391 974 B1 | 12/1988 | A61K/35/16 |
| WO | WO 85/01941 | 5/1985 | C07G/7/00 |
| WO | WO 89/05652 | 6/1989 | A61K/37/02 |

OTHER PUBLICATIONS

Suomela, Hannu., "Human Coagulation Factor IX", Eur. J. Biochem., vol. 71, pp. 145–154, 1976.*
Suomela, Hannu, "Multiple Forms of Human Factor IX in Chromatography and Isoelectric Focusing", Thrombosis Research, vol. 7, pp. 101–112, 1975.*
Harris et al. Proteins Prufication Methods. Oxford: Irl Prss. 1989. pp. 238–242, 1989.*
Cash, et al., Thrombos. Diathes. haemorrh. 33:632–639 (1975).
Feldman, et al., Biotech. Blood Prot. 227:63–68 (1993).
Josic, et al., J. Chrom. 632:1–10 (1993).
Liebman, et al., Proc. Natl. Acad. Sci. U.S.A. 82:3879–3883 (1985).
Osterud, et al., J. Biol. Chem. 253(17):5946–5951 (1978).
Pejaudier, et al., Vox Sang. 52:1–9 (1987).
Pittman, et al., Blood 79:389–397 (1992).
Reekers, et al., Haemostasis 1:2–22 (1972).
Roberts, et al., Vox Sang. 67(Sup. 1):69–71 (1994).
Suomela, Eur. J. Biochem. 71:145–154 (1976).
Suomela, Thrombos, Haemostas. 35:211–221 (1976).
Suomela, Thromb. Res. 7:101–112 (1975).
Yan, et al., Biotechnology 8:655–661 (1990).

* cited by examiner

Primary Examiner—Brenda Brumback
Assistant Examiner—Anish Gupta
(74) Attorney, Agent, or Firm—Ivor R. Elrifi; Mintz, Levin, Cohn, Ferris, Glovsky and Popeo, P.C.

(57) ABSTRACT

Provided by the present invention are novel methods of factor IX protein recovery and purification.

6 Claims, No Drawings

FACTOR IX PURIFICATION METHODS

This application is a continuation, of application Ser. No. 08/472,823, filed Jun. 7, 1995, now U.S. Pat. No. 5,714,583.

FIELD OF INVENTION

The present invention relates generally to novel protein recovery and purification methods and more specifically to novel methods for the recovery and purification of factor IX.

BACKGROUND OF THE INVENTION

The advent of recombinant technology now allows for the production of high levels of proteins within suitably transformed host cells. For secreted proteins, purification of the protein of interest involves isolation and purification from the host cell culture medium. Typically, the culture medium contains selected nutrients (e.g. vitamins, amino acids, cofactors, minerals,) and additional growth factors/supplements including insulin and possibly additional exogenous proteins. Conditioned medium contains not only the secreted product of interest, but also significant quantities of additional secreted host cell proteins and other substances (e.g. nucleic acids, membrane vesicles). Although expressed at high levels, the product of interest may represent a minority of all proteins present in conditioned medium. Not unexpectedly, proteins secreted by transformed host cells may possess characteristics quite different from those of the product of interest (e.g. charge, molecular size, amino acid composition). Similarly, selected secreted host cell proteins may exhibit properties very similar to those of the product of interest, thereby placing significant burden on the process used for purification. While developing a process for purification of a recombinant protein from conditioned medium, it is important that conditions used be limited with respect to denaturation of the product of interest (conditions which could be used to exploit minor differences between secreted proteins for major benefit to separation), thereby making it difficult to separate the product of interest from all other host cell proteins present.

In addition to secreted host cell proteins described above, conditioned medium may also contain products derived from the heterologously-expressed gene coding for the product of interest. These are not desirable for the final drug substance and include, for example, product forms lacking certain post-translational modifications such as glycosylation, sulfation, gamma carboxylation, or other modification potentially necessary for biological activity. In addition, proteolytically-degraded forms of the product of interest may be present in conditioned medium which also need to be removed during purification, but which very closely resemble the product of interest. Unfortunately, most approaches, such as ion exchange chromatography, hydrophobic interaction chromatography, and size exclusion chromatography may not provide the extent of resolution of the product of interest necessary for use in human therapeutic situations from these undesired forms. To take full advantage of minor differences between the desired product and contaminants (e.g. small charge differences, small differences in molecular size) the use of strong denaturants is often required. Such denaturants, however, can lead to loss of biological activity, expression of neoantigenic sites, and potentially enhance chemical decomposition of selected post-translational modifications.

In addition to separating the product of interest from molecules with similar properties (e.g. modified forms of the expressed gene), it is also important to recognize the need to separate the desired product from components present in conditioned medium with which it specifically interacts. Where the protein of interest is positively charged, it will tend to bind to any negatively charged molecules present thereby making purification of the protein by traditional methods very difficult.

Of general background interest to the present invention are the following. Yan, U.S. Pat. No. 4,981,952 (Jan. 1, 1991) and Yan, etal. Bio/Technology 8:655 (July 1990) which disclosed the use of pseudo-affinity anion exchange chromatography for the purification of vitamin K-dependent proteins. Josic, et al. J. Chrorn. 632:1 (1993) disclosed the use of heparin affinity chromatography to resolve factor IX from other vitamin K-dependent proteins. Suomela. Thromb. Res. 7:101 (1975); Suomela, Eur. J. Bio. Chem. 71:145 (1976); and Suomela, Thrombos. Haemostis. 35:211 (1976) described the use of hydroxyapatite in the separation of various clotting factors and factor IX plasma variants (based on charge differences due to variation in content of carbohydrate moieties, for example, sialic acid and galactose). However, Reekers, et al. Haemostasis 1:2 (1972) demonstrated the inability of hydroxyapatite to separate factors II, VII and IX from each other and from other plasma proteins. Schwinn, et al. U.S. Pat. No. 4,411,794 disclosed the partial purification of blood clotting factors using hydroxyapatite in the presence of calcium at a concentration of 50–200 mM. Feldman, et al. Biotech. Blood Proteins 227:63 (1993) and Roberts, et al. Vox Sang 67(suppl. 1): 69 (1994) disclosed the reduction of viral infectivity using acidification and copper-charged chelating Sepharose which resulted in low factor IX yields from human plasma.

Typically, researchers have used combinations of traditional chromatographic techniques to purify desired products. Often times, such techniques are not sufficient for purification of a product to the level of purity and consistency desired for a human therapeutic product. Researchers have attempted to overcome this difficulty by use of affinity chromatography wherein a protein of interest is bound to an immobilized ligand with which it interacts specifically. Following appropriate washing, the desired product can be eluted by disruption of the ligand-protein interaction, often resulting in a significantly more pure eluate. However, in the instance of separation of a desired product from modified forms present in conditioned medium, single step affinity chromatographic techniques may not be sufficient, and must be used in conjunction with other affinity resins and/or traditional separation techniques. Even high resolution affinity chromatography steps (e.g., immunoaffinity purification using an immobilized monoclonal antibody) may not afford sufficient resolution of the desired product from other components due to common sites of interaction (e.g., where an epitope which is present in the product of interest, is present as well in a proteolytically-degraded form of the product).

Accordingly, there continues to exist a need in the art for protein purification methods that effectively overcome such difficulties.

BRIEF SUMMARY OF THE INVENTION

Provided by the present invention are methods for the purification of factor IX in a solution comprising the steps of applying the solution containing factor IX to an anion exchange resin, washing said anion exchange resin with a solution having a conductivity that is less than required to elute factor IX from the resin, eluting said anion exchange resin with a first eluant to form a first eluate, applying said eluate to a heparin or heparin-like (e.g., negatively charged matrix) resin, eluting said heparin or heparin-like resin with a second eluant to form a second eluate, applying said second eluate to an hydroxyapatite resin, and then eluting said hydroxyapatite resin with a third eluant to form a third eluate containing the purified factor IX. Optionally, the first eluate can be applied to an hydroxyapatite resin. As yet another option, the method comprises the further steps of applying the third eluate to an immobilized metal affinity resin, and then eluting the immobilized metal affinity resin with a fourth eluant to form a fourth eluate containing the purified factor IX. According to the methods of the invention, the factor IX can be either plasma-derived, expressed by cells in culture, or recombinantly produced as is known to one skilled in the art. Preferably, the first wash comprises a solution having a conductivity that is less than required to elute factor IX from the column and is generally greater than or equal to the conductivity of the load solution and of the first eluant buffer; this conductivity is sufficient to remove a substantial proportion of those contaminating proteins that would otherwise be present in the first eluate. A suitable first wash comprises a salt solution such as sodium chloride, potassium chloride, sodium sulphate, sodium phosphate, or potassium phosphate, and optionally, may contain a suitable buffering agent. Suitable concentration ranges are those which are effective in removing contamininants without eluting factor IX and include for example 25 mM to 200 mM salt, and preferably is 200 mM sodium chloride. The first eluant comprises a divalent cation such as calcium, magnesium, manganese, strontium, zinc, cobalt, and nickel; suitable concentration ranges are those which are effective in eluting factor IX, including for example a solution containing a buffering agent at pH about 8.0 such as Tris, in the range of 5 to 100 mM, preferably approximately 50 mM, a salt such as NaCl in the range of 50 to 250 mM, preferably 100 mM, and calcium chloride in the range of 5 to 20 mM, preferably approximately 10 mM.

Suitable anion exchange resins include those resins having a positively charged group such as diethyleaminoethane (DEAE), polyethyleneimine (PEI), and quaternary aminoethane (QAE) and include Q-Sepharose Fast Flow, DEAE-Sepharose Fast Flow, POROS-Q, Fractogel-TMAE, Fractogel-DMAE, and QAE-Toyopearl, with the preferred resin being Q-Sepharose Fast Flow (Pharmacia).

The second eluant can be a suitable salt in buffer, such as Tris with sodium chloride and potassium chloride, with 50 mM TRIS, 0.50 M NaCl, pH 8.0 being preferred. Suitable heparin or heparin-like resins include those resins having a negatively charged group such as heparin, sulfated esters of cellulose, sullfylpropyl (SP), carboxyl, and carboxy methyl and include Matrex Cellufine Sulfite, Heparin Sepharose, Heparin Toyopearl, Carboxy Sulfon, Fractogel EMD-SO$_3$, and Fractogel-EMD COO, with the preferred being Matrex Cellufine Sulfate.

The third eluant can be a salt, such as phosphate and sulphate, with 0.5 M potassium phosphate, 0.2 M NaCl, pH 7.2 preferred. Suitable hydroxyapatite resins include any containing calcium-phosphate such as ceramic-Hy (droxyapatite, Biogel HT, and others, with ceramic-HA preferred. The immobilized metal affinity resin can be one such as Fractogel-EMD-Chelate, Chelating-Sepharose, Matrex Cellufine Chelate, and POROS 20 MC, with Fractogel EMD-Chelate currently preferred. The fourth eluant is a buffer solution containing a chelator such as imidazole, EDTA, EGTA, glycine, histidine, and Tris, with the preferred being 20 mM potassium phosphate, 15 mM imidazole, 0.1 M NaCl, pH 7.1.

Also provided by the present invention are factor IX compositions produced by the methods of the invention. The factor IX so produced has a specific activity in the range of 240–400 U/mg, and is optionally about 240 U/mg.

DETAILED DESCRIPTION OF THE INVENTION

As used herein, the term "factor IX" includes, but is not limited to factor IX isolated from plasma, transformed cell lines, and recombinantly produced factor IX isolated from host cell culture medium.

As used herein, the term "anion exchange resin" includes, but is not limited to resins having a positively charged moiety (at neutral pH), such as diethyleaminoethane (DEAE), polyethyleneimine (PEI), and quaternary aminoethane (QAE) and includes, for example, Q-Sepharose Fast Flow (Pharmacia), DEAE-Sepharose Fast Flow, DEAE-Toyopearl, QAE-Toyopearl, POROS-Q, Fractogel-DMAE, Fractogel EMD-TMAE, Matrex Cellufine DEAE and the like.

As used herein, the term "first wash" includes, but is not limited to a solution having a conductivity that is less than required to elute factor IX from the anion exchange column and whose conductivity is generally greater than or equal to the conductivity of the load solution and of the conductivity of the first eluant; this conductivity is sufficient to remove a substantial proportion of those contaminating proteins that would otherwise be present in the eluate. As one skilled in the art readily appreciates, the first wash can be any salt solution and includes, for example, sodium chloride, potassium chloride, sodium sulphate, sodium phosphate, or potassium phosphate, and can be suitably buffered. Typically, concentrations range from low (25 mM salt) to high (200 mM salt), with 200 mM sodium chloride presently preferred.

As used herein, the term "first eluant" includes, but is not limited to solutions composed of a buffering agent (e.g. Tris) at a concentration of approximately 0.05 M, salt (e.g. NaCl) at a concentration which is not sufficient for elution from the resin in the absence of divalent cation (e.g. approximately 0.10 M–0.20 M), and divalent cation (e.g. CaCl$_2$) at low concentrations of approximately 0.01 M, at pH 8.0. The selection of buffer composition is compatible with the presence of divalent cation. Preferably, the "first eluant" has a lower conductivity than the "first wash".

As used herein, the terms "heparin" resin and "heparin-like" resin are used interchangeably, and include but are not limited to, resins containing an immobilized negatively charged moiety such as heparin, sulfated esters of cellulose, sulfylpropyl (SP), carboxyl, and carboxy methyl and includes Fractogel-EMD-SO$_3$, Carboxy Sulfon, Fractogel-EMD-COO, Heparin-Sepharose, and Matrex Cellutfine Sulfate.

As used herein, the term "second eluant" includes, but is not limited to: solutions composed of a buffering agent (e.g. Tris) at a concentration of approximately 0.05 M, and salt (e.g. NaCl, KCl, Na$_2$SO$_4$) at a concentration sufficient to disrupt the interaction of factor IX with the negatively-charged resin support (e.g. 0.50 M) at approximately pH 8.0. As used in this process, the second eluant should be compatible with the subsequent process step, i.e., hydroxyapatite.

As used herein, the term "hydroxyapatite column" includes, but is not limited to: calcium phosphate gel supports including for example, BioGel-HT, and Ceramic-hydroxyapatite.

As used herein, the term "third eluant" (and "second phosphate buffer") includes, but is not limited to: solutions composed of a buffering agent (e.g. phosphate or sulfate) at concentrations sufficient to disrupt interaction of factor IX with the resin (e.g. approximately 0.20 M or higher) and salt (e.g. NaCl, KCl) present at concentrations sufficient to minimize charge-interactions of the factor IX with the hydroxyapatite resin, at approximately neutral pH (pH 7.2); the term "first phosphate buffer" includes but is not limited to solutions composed of a buffering agent (e.g., phosphate or sulfate) at concentrations sufficient to remove inactive forms of factor IX from the hydroxy-apatite resin.

As used herein, the term "immobilized metal affinity resin" (IMAC) includes, but is not limited to: resins containing an immobilized functional moiety (e.g. iminodiacetic acid) capable of binding and coordinating multivalent cations including Chelating-Sepharose, Fractogel-EMD-Chelate, POROS 20 MC, and Matrex Cellufine Chelate. The bound metal ion can be selected from several possible choices including but not limited to copper, nickel, cadmium, cobalt, iron, zinc, or strontium.

The term "fourth eluant" (also termed "displacer") includes but is not limited to, any compound which will displace bound factor IX from the IMAC resin support, while minimizing displacement of the immobilized metal ion from the resin support, and includes but is not limited to such compounds as glycine, histidine, tris, imidazole, EDTA, EGTA, and the like. As one skilled in the art readily appreciates, the appropriate concentration of displacer will vary according to binding affinity and can be ascertained by experimental evaluation of conditions. Typically, concentrations range from low (e.g. 5–15 mM displacer) to high (e.g. 100–200 mM displacer).

Reference to factor IX specific activity of "U/mg" includes but is not limited to: biological activity determined in the in vitro (APTT) clotting assay using pooled plasma or isolated, purified factor IX as standard. The concentration of protein can be determined by any of several appropriately validated methods including SEC, RP-HPLC, dye-based assays (e.g., Bradford, Lowry) or absorbance at 280 nm. Factor IX activity is determined according to the method of Pittman, D., et al., Blood 79:389-397 (1992) utilizing factor IX-deficient plasma.

FIG. 1 provides an overview of the process. While the order of the steps set forth is the presently preferred embodiment, it will be appreciated by one skilled in the art that the order can be re-configured if desired and that steps can be omitted.

According to the present invention, cells are first removed from conditioned medium, e.g. by microfiltration (MF) utilizing tangential flow filtration membranes with pore size of approximately 0.6 μm. Optionally, cell-free conditioned medium is prepared for purification by filtering through a 0.45 μm depth filter. The cell-free conditioned medium can then be concentrated by ultrafiltration, if desired, followed by diafiltration into an appropriate buffer for loading onto the first chromatographic step. Alternatively, the cell-free conditioned medium may be loaded directly onto the first chromatography column equilibrated in an appropriate buffer.

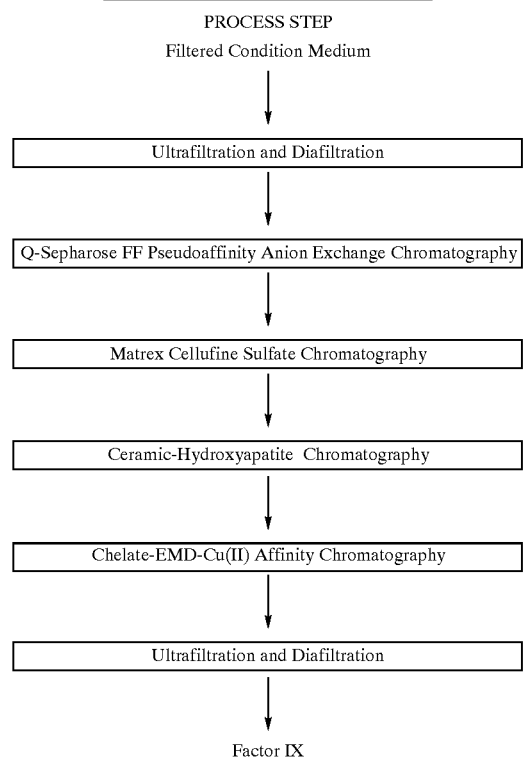

FIGURE 1
Overview of factor IX Purification Process

The initial process step, UF/DF#1, entails concentration of the cell-free factor IX-containing conditioned media by ultrafiltration, followed by diafiltration. Although not required for binding of factor IX to the first chromatography column, this step is effective in removing small-molecular-weight cell culture media components. Such components may bind to the initial chromatography column, thereby decreasing the capacity of the column for factor IX. UF/DF#1 is used to exchange the factor IX into an appropriate buffer solution for subsequent processing.

In the first chromatography step, anion-exchange on Q-Sepharose Fast Flow (FF) (Pharmacia), the factor IX is captured and purified from host-cell components present in the UF/DF #1 concentrated pool. The Q-Sepharose FF column adsorbs the factor IX protein, and contaminating host-cell proteins with isoelectric points greater than the operating pH are removed from the process stream by flowing through the column. The column to which factor IX is adsorbed is then washed prior to elution to remove loosely-bound contaminants and adjust the conductivity of the buffer in preparation for elution.

Typically, bound proteins are eluted from Q-Sepharose FF by increasing the ionic strength of the buffer. The factor IX purification process, however, employs this resin in a pseudo-affinity anion-exchange mode in which active factor IX is eluted by addition of e.g., calcium chloride to the buffer. This divalent cation results in elution of active forms of factor IX from the resin. Some less active forms of factor IX may also elute from the Q-Sepharose FF column with this elution buffer. Selected inactive forms of factor IX and other, contaminating host-cell proteins remain bound to the column. The Q-Sepharose FF step achieves a significant increase in the purity of the factor IX.

In the second chromatography step, the Q-Sepharose FF elution pool is loaded directly, without dilution, onto the Matrex Cellufine Sulfate column. The factor IX adsorbs to the column, while other, contaminating proteins (e.g., soluble PACE and other host-cell proteins present in the Q-Sepharose FF eluate) are removed from the process stream by flowing through the column. The column is washed with a low-ionic-strength buffer to remove all non-binding proteins. The factor IX is eloted by an increase in the ionic strength of the buffer, using salt (e.g., sodium chloride).

Further removal of inactive factor IX forms is obtained during the third chromatography step, Ceramic-HA column chromatography. The pH of the Matrex Cellufine Sulfate elution pool is adjusted to approximately 7.5, and the elution pool is then loaded directly onto the Ceramic-HA column. The factor IX is adsorbed by the column. The Ceramic-HA column is washed with buffer to remove loosely bound contaminants, followed by a wash with 50 mM potassium phosphate, 0.185 M NaCl (pH 7.2) to remove more tightly bound contaminants, including inactive forms of factor IX. Bound, active factor IX is eluted in a step-wise manner using a solution containing a higher concentration of potassium phosphate (e.g. 200 mM or greater, pH 7.2) as the eluant.

The fourth chromatography step, Fractogel EMD-Chelate -Cu(II) chromatography, removes low levels of contaminating host-cell proteins still present in the product stream. The Ceramic-HA elution pool is loaded directly onto the Fractogel EMD-Chelate -Cu(II) column. Factor IX and a number of contaminating, proteins are adsorbed to the column. Purified active factor IX is eluted from the column by low concentrations of imidazole (e.g. approximately 15 mM) in the buffer, and the residual, contaminating host-cell proteins are removed from the product stream by remaining bound to the column.

Finally, the Fractogel EMD-Chelate -Cu(II) elution pool is concentrated by ultrafiltration, followed by diafiltration (UF/DF#2) into a buffer identical to a formulation buffer except that it does not contain polysorbate 80. A suitable formulation buffer comprises histidine, glycine, sucrose, and polysorbate-80 optionally at 10 mM, 260 mM, 1%, and 0.005%, respectively. Upon completion of the diatfiltratiun, factor IX is concentrated to achieve a target concentration. The product pool is removed from the UF/DF 2, apparatus and formulated by addition of polysorbate 80 to a target concentration of 0.005%. The factor IX drug substance is then filtered (0.2 μm), sampled, labeled. and stored frozen at approximately −80° C. The last process step, UF/DF#2, is effective in concentrating and diafiltering the purified factor IX drug substance without significant protein denaturation or loss. SDS-PAGE analysis (reduced and nonreduced) is one method used to evaluate overall process performance. Each step provides greater than 80% to 100% yield and the average overall yield of factor IX is about 51%. The overall process yield is tleterminedl from the clotting activity entering the purification process and the total clotting activity in the factor IX drug substance (excluding material removed as in-process samples and retains).

The following examples illustrate practice of the invention. These examples are for illustrative purposes only and are not intended in any way to limit the scope of the invention claimed.

Example 1 describes concentration of protein by ultrafiltration/cliatfiltration; Example 2 relates to purification of factor IX by pseudo-affinity anion-exchange chromatography on Q-sepharose fast flow; Example 3 describes puriciaztiton of factor IX by chromatography on Matrex Celluftine Sulfate; Example 4 relates to purification of protein with hydroxyapatite chromatography; Example 5 describes purification of protein by immbobilized metal affinity chromatography; and Example 6 relates to concentration and formulation of protein by ultrafiltration/diafiltration.

EXAMPLE 1

Concentration of Protein by Ultrafiltration/Diafiltration

Optionally, ultrafiltration/diafiltration (UFIDF#1) can be performed to concentrate and to buffer-exchange the cell-free conditioned medium using tangential-flow membrane filtration. The membrane used in the tangential-flow device serves as a selectively permeable filter that separates substances on the basis of molecular weight. Solution components of high molecular weight, such as factor IX, are retained by the membrane, and components of low molecular weight, such as inorganic salts and buffer components, pass freely through the porous membrane structure and are removed in the permeate.

When buffer is drawn from the tangential-flow device at a rate faster than that at which replacement buffer is added to the retentate, the protein solution is concentrated. When replacement buffer is added to the tangential-flow retentate at a rate approximately equal to the rate at which the buffer is drawn through the membrane, the initial buffer is continuously diluted (protein diafiltration). Under these conditions, compounds of low molecular weight are readily exchanged and the protein concentration remains constant. The addition of five retentate volumes of buffer results in a theoretical replacement of $\geq 99\%$ of the initial buffer.

Before use, the UF/DF#1 system is equilibrated with 50 mM TRIS, 150 mM NaCl, pH 7.5. The cell-free conditioned medium is concentrated approximately 20-fold relative to the initial volume of the cell-free conditioned medium. The concentrated cell-free conditioned medium is then diafiltered into the buffer. The diafiltration is complete when at least five retentate volumes of the buffer have passed through the membrane, resulting in a theoretical removal of $\geq 99\%$ of salts and other low-molecular-weight components present in the cell-free conditioned medium.

Once diafiltration has been completed, the retentate is concentrated if necessary. The equipment is then flushed with sufficient buffer to recover residual factor IX product from the reservoir and tubing. The pool is then pumped out of the UF/DF vessel and filtered through an autoclaved 0.2-μm filter into a clean vessel. The UF/DF#1 pool is stored at 2 to 8° C. until it is further processed.

EXAMPLE 2

Purification of Factor IX by Pseudo-Affinity Anion-Exchange Chromatogarphy on Q-Sepharose Fast Flow Q-Sepharose Fast Flow (FF) (Pharmancia) is a strong anion-exchange resin composed of a cross-linked agarose matrix that is covalently derivatized with a quaternary amine group through a short linker. Acidic proteins (such as factor IX) and other polyionic substances with a net negative charge at the pH of operation bind to Q-Sepharose FF via charge interactions. Typically, bound components are differentially eluted from Q-Sepharose FF by disruption of these charge interactions with solutions of increased conductivity. However, the factor IX purification process employs the Q-Sepharose FF resin in a pseudo-affinity mode. Factor IX is eluted from the column using a solution containing low-concentration (10 mM) calcium chloride. The inclusion of calcium ions in the elution buffer causes a conformational change in the factor IX that results in elution from the resin.

Q-Sepharose FF is used to capture factor IX from UF/DF#1 retentate; to remove uncharged and basic contaminants from the process stream (in the unbound fraction during loading of the column); to separate factor IX from acidic proteins (which bind to the resin but are not eluted by addition of calcium chloride to the buffer), including inactive forms of factor IX; and to deliver a concentrated factor IX process stream into the subsequent purification process chromatography step, Matrex Celluftine Sulfate.

Optionally, all chromatography operations for this step are performed at 2° to 8° C. The Q-Sepharose FF column is first charged with 50 mM TRIS, 2 M NaCl, pH 8.0, followed by equilibration with 50 mM TRIS, 150 mM NaCl, pH 8.0. The UF/DF#1 retentate is loaded onto the Q-Sepharose FF column, and the column is then washed with 50 mn. TRIS, 200 mM NaCl, pH 8.0. This first wash ensures that the entire load has passed through the column and that non-adsorbing impurities in the load, as well as contaminants that are loosely bound to the resin, have been washed from the system. The column is then washed with 50 mM TRIS, 100 mM NaCl, pH 8.0 to lower the conductivity in preparation for elution.

Factor IX is eluted from the column with 50 mM TRIS, 100 mM NaCl. 10 mM $CaCl_2$, pH 8.0, and the eluted product is collected as a single peak. The Q-Sepharose FF eluate is sampled and stored at 2 to 8° C. until it undergoes further processing. Optionally, the column can be regenerated and reused.

EXAMPLE 3

Purification of Factor IX by Chromatography on Matrex Cellufine Sulfate

Matrex Cellufine Sulfate is composed of spheroidal cellulose beads derivatized with sulfate esters. It can be used as an immobilized heparin analogue for affinity-purification of proteins containing heparin-bindin domains. It can also be used for cation-exchange chromatography because of its negatively charged sulfate functions. Basic proteins, other polyionic substances with a net positive charge at the pH of operation, and heparin-binding proteins bind to the resin and are eluted with solutions of increasing ionic strength. The Matrex Cellufine Sulfate resin is used in the factor IX purification process for removal of host-cell proteins other than factor IX in the Q-Sepharose FF elution pool and, optionally, to provide appropriate buffer conditions for loading the hydroxyapatite column.

Optionally, all chromatography operations for this step are carried out at 2 to 8° C. In preparation for the load step, the Matrex Cellufine Sulfate column is equilibrated with 50 mM TRIS, pH 8.0. The Q-Sepharose FF elution pool is loaded directly onto the equilibrated Matrex Cellufine Sulfate column, the column is washed with 50 mM TRIS, 150 mM NaCl, 10 mM $CaCl_2$, pH 8.0 to ensure that all of the load has passed through the column and that weakly bound impurities are removed from the system. Next, the column can be washed to remove calcium ions prior to elution.

After the wash steps have been completed, the Matrex Cellufine Sulfate column is eluted with 50 mM TRIS, 500 mM NaCl, pH 8.0, and the eluate collected as a single UV-absorbing elution pool. The Matrex Cellufine Sulfate elution pool is sampled and stored at 2° to 8° C. until it is further processed. Optionally, the column can be regenerated and reused.

EXAMPLE 4

Purification of Protein with Hydroxyapatite Chromatography

Ceramic-Hydroxyapatite (Ceramic-HA) is a synthetic form of calcium phosphate consisting of spheroidal macroporous particles with high mechanical strength. Ceramic-HA separates proteins with a wide range of charges and isoelectric points largely on the basis of charge interactions. Factor IX is an acidic protein that binds to Ceramic-HA at approximately neutral pH. Typically, acidic proteins are eluted from Cerainic-HA by the addition of phosphate to the buffer solution. The concentration of phosphate required for elution varies, depending upon the properties of the molecule of interest, thereby allowing differential elution of bound proteins. Ceramic-HA is used in the factor IX purification process to remove inactive factor IX, and other contaminants in the Matrex Cellufine Sulfate elution pool and to exchange the eluate buffer to one compatible with the final chromatographic step. Because the final chromatography step is immobilized metal affinity chromatography, the buffers used for elution of Ceramic-HA are selected to be compatible with IMAC. This avoids an in-process diafiltration or other buffer exchange procedure. Buffers such as Tris, glycine, histidine are not compatible with IMAC because of disruption of the metal ion-immobilized ligand interaction. Elution of the Ceramic-HA column with phiosphliate buffers avoids such complications.

In preparation for loading, the Ceramic-HA column is equilibrated with 50 mM TRIS, 500 mM NaCl, pH 7.5. The Matrex Cellutine Sulfate elution pool is titrated to pH 7.5 with dilute HCl and loaded directly onto the Ceramic-HA column. Upon completion of loading, the column is washed with buffer (0.5 M NaCl, 50 mM TRIS, pH 7.5) to ensure that all of the load has passed through the column and that loosely bound contaminants are removed from the column. Next, the column is washed with 50 mM $K_2HPO_4$, 185 mM NaCl, pH 7.2 to remove inactive forms of factor IX from the process stream.

Upon completion of the wash steps, the bound factor IX is eluted with 500 mM $K_2HPO_4$, 200 mM NaCl, pH 7.2, and the factor IX eluate is collected as a single UV-absorbing elution pool. The eluate pool is sampled and stored at 2 to 8° C. until it undergoes further processing. Optionally, the column can be regenerated and reused.

EXAMPLE 5

Purification of Protein by Immobilized Metal Affinity Chromatography

Fractogel-EMD-Chelate is composed of a methacrylate polymer derivatized with iminodiacetic functional groups to which transition-state metal ions can be bound. In preparation for use in the purification process, the resin is charged with copper ions using a solution of copper sulfate. Proteins capable of interacting with the immobilized copper ions are retained on the column, and non-interacting contaminants pass through in the unbound fraction. Bound proteins are eluted from the resin using solutions containing imidazole. A Fractogel-EMD-Chelate-Cu(II) step can be used in the protein purification process to remove from the process stream contaminants that do not bind to the immobilized metal ion or that require higher concentrations of imidazole for elution than those required by factor IX. The term IMAC (immobilized metal affinity chromatography) is also used to denote this chromatography step.

In preparation for loading, the uncharged (no immobilized metal ion) Fractogel-EMD-Chelate column is washed with 100 mM acetic acid, 500 mM NaCl, pH 4.0 and is subsequently charged with 200 mM $CuSO_4$, 500 mM NaCl. Loosely bound copper ions are removed by washing the charged resin with 100 mM acetic acid, 500 mM NaCl, pH 4.0, followed by 200 mM imidazole, 500 mM NaCl, pH 7.1. The Fractogel-EMD-Chelate-Cu(II) resin is then equilibrated in 200 mM $K_2HPO_4$, 200 mM NaCl, pH 7.1 (Equilibration V). The Ceramic-HA elution pool is loaded directly onto the equilibrated Fractogel-EMD-Chelate-Cu(II) column.

Upon completion of loading, the column is washed with equilibration buffer to ensure that all of the load has passed through the column. Factor IX bound to the resin is eluted using 20 mM $K_2HPO_4$, 15 mM imidazole, 100 mM NaCl, pH 7.1. The Fractogel-EMD-Chelate-Cu(II) eluate is collected as a single UV-absorbing pool. After collection. the elution pool is diluted with 20 mL of 500 mM EDTA, pH 8.0 per liter of column eluate. The diluted elution pool is stored at room temperature until it undergoes further processing.

EXAMPLE 6

Concentration and Formulation of Protein by Ultrafiltration/Diafiltration #2

To transfer the factor IX to a buffer of choice, a combination ultrafiltration/diafiltration step is used. Tangential-flow UF/DF is a non-chromatographic separation method that can be used to concentrate and buffer-exchange substances in solution. A feedstream is directed parallel to the surface of a selectively permeable membrane, and pressure is applied to the retentate side of the membrane outlet to effect transport of water and solutes at the membrane surface on the basis of their relative permeability. Under these circumstances, low-molecular-weight feedstream components pass freely through the membrane pores into the permeate fraction, and higher-molecular-weight substances (e.g., factor IX) are retained by the membrane and constitute the retentate fraction. In this manner, water and buffer salts can be removed from the Fractogel-EMD-Chelate-Cu(II) elution pool, and the factor IX can be concentrated to a target concentration.

Optionally, a spiral-wound cartridge component of the tangential-flow system is first equilibrated with 10 mM histidine, 260 mM glycine, 1% sucrose, pH 6.8. The Fractogel-EMD-Chelate-Cu(II) elution pool (previously diluted with 500 mM EDTA) is then transferred to the stainless-steel retentate pressure vessel of the tangential-flow apparatus in preparation for protein concentration.

After the transfer is completed, the retentate solution is pumped continuously from the pressure vessel through the spiral-wound cartridge and hack to the pressure vessel under a net positive transmembrane pressure. The volume of the retentate is monitored continuously during this operation by measuring the permeate fraction volume using a graduated collection vessel.

When the target retentate volume is reached, the retentate pool is diafiltered into the buffer of choice. During this operation, diafiltration buffer is pumped into the pressure vessel at the same rate at which permeate flows from the system, thereby maintaining a constant retentate volume.

After completion of the diafiltration step, the retentate fraction is concentrated to a target volume using ultrafiltration. The outflow fraction from the retentate pressure vessel is stopped, and the retentate fraction in the spilal-wound cartridge is flushed into the retentate pressure vessel with a target volume of the buffer of choice. The concentrated, diafiltered factor IX product is recovered from the pressure vessel by pumping into tared pool bottles.

The factor IX product pool is diluted with 10 mM histidine, 260 mM glycine, 1% sucrose, 1% polysorbate 80, pH 6.8 to a final concentration of 0.005% polysoirbate 80. The product is then mixed thoroughly and filtered through a 0.2-$\mu$m filter (previously equilibrated in 10 mM histidine, 260 mM glycine, 1% sucrose, 0.005% polysorbate 80, pH 6.8 into depyrogenated Teflon bottles. The protein is then sampled, labeled, frozen quickly in liquid nitrogen, and stored at $-80°$ C.

While the present method of the invention is exemplified by purification of recombinantly-produced factor IX from transformed host cells, the method is also amenable to purification of factor IX naturally occurring within a cell and can be used to purify proteins from solution or from plasma, cell homogenates, cell culture supernatants, or isolated cellular sub-fractions. While the present invention has been described in terms of specific methods and compositions, it is understood that variations and modifications will occur to those skilled in the art upon consideration of the present invention.

Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

What is claimed:

1. A method for separating active recombinant factor IX from a composition comprising inactive recombinant factor IX comprising the steps of:
   (A) applying said composition to an hydroxyapatite resin,
   (B) washing said hydroxyapatite resin with a first buffer, wherein said first buffer has a salt concentration sufficient to remove said inactive factor IX, and
   (C) eluting said hydroxyapatite resin with a second buffer, wherein said second buffer has a salt concentration sufficiently high to elute said active factor IX.

2. The method of claim 1, wherein said first buffer and said second buffer is a phosphate buffer.

3. The method of claim 1, wherein said first phosphate buffer is 50 mM potassium phosphate, 0.185 M NaCl, pH 7.2 and said second phosphate buffer is 0.5 M potassium phosphate, 0.2 M NaCl, pH 7.2.

4. A method for separating active recombinant factor IX from a composition comprising inactive recombinant factor IX comprising the steps of:
   (A) applying said composition to an hydroxyapatite resin,
   (B) washing said hydroxyapatite resin with a first buffer, wherein said first buffer has a salt concentration sufficient to remove said inactive factor IX, but low enough that active factor IX is not removed, and
   (C) eluting said hydroxyapatite resin with a second buffer, wherein said second buffer has a salt concentration sufficiently high to elute said active factor IX.

5. The method of claim 4, wherein said first buffer and said second buffer is a phosphate buffer.

6. The method of claim 4, wherein said first phosphate buffer is 50 mM potassium phosphate, 0.185 M NaCl pH 7.2 and said second phosphate buffer is 0.5 M potassium phosphate, 0.2 M NaCl, pH 7.2.

* * * * *